United States Patent
de Bruin et al.

(10) Patent No.: US 6,767,517 B2
(45) Date of Patent: Jul. 27, 2004

(54) METHOD AND APPARATUS FOR THE CONTINUOUS PRODUCTION OF DIARYL CARBONATES

(75) Inventors: Philip R. de Bruin, Leeuwarden (NL); James S. Law, Leidschendam (NL); Vincentius Antonius Vriens, Hillegom (NL)

(73) Assignee: General Electric Company, Schenectady, NY (US)

(*) Notice: Subject to any disclaimer, the term of this patent is extended or adjusted under 35 U.S.C. 154(b) by 490 days.

(21) Appl. No.: 09/824,886

(22) Filed: Apr. 3, 2001

(65) Prior Publication Data

US 2001/0021786 A1 Sep. 13, 2001

Related U.S. Application Data

(62) Division of application No. 09/457,320, filed on Dec. 8, 1999, now Pat. No. 6,294,684.

(51) Int. Cl.$^7$ .............................. B01J 8/00; B01D 3/14; B01D 3/34
(52) U.S. Cl. ...................... 422/188; 422/187; 422/189; 202/153; 202/158; 203/28; 203/DIG. 6
(58) Field of Search ................................ 422/187–189, 422/193, 195, 190; 558/274, 270, 260; 202/154, 155, 153, 158; 203/28, 29, DIG. 6, 98, 100

(56) References Cited

U.S. PATENT DOCUMENTS

| | | | |
|---|---|---|---|
| 4,218,391 A | 8/1980 | Romano et al. | |
| 4,318,862 A | 3/1982 | Romano et al. | |
| 4,948,871 A | 8/1990 | Fukuoka et al. | |
| 5,210,268 A | 5/1993 | Fukuoka et al. | |
| 5,210,269 A | 5/1993 | Di Muzio et al. | |
| 5,344,954 A | 9/1994 | Schon et al. | |
| 5,426,207 A | * 6/1995 | Harrison et al. | 558/274 |
| 5,478,962 A | 12/1995 | De Nardo et al. | |
| 5,498,319 A | 3/1996 | Ehlinger | |
| 5,523,451 A | * 6/1996 | Rechner et al. | 558/270 |
| 5,527,943 A | 6/1996 | Rivetti et al. | |
| 5,536,864 A | 7/1996 | Paret et al. | |
| 5,705,673 A | 1/1998 | Rivetti et al. | |

FOREIGN PATENT DOCUMENTS

| | | |
|---|---|---|
| EP | 461 274 | 12/1990 |
| EP | 582 930 | 8/1993 |
| EP | 582 931 | 8/1993 |
| EP | 0633241 B1 | 1/1995 |
| EP | 0722931 | 7/1996 |
| EP | 0781760 | 7/1997 |
| EP | 781760 | 7/1997 |
| EP | 785184 | 7/1997 |
| JP | 61172852 | 8/1986 |
| JP | 62277345 | 12/1987 |
| JP | 11012230 | 1/1999 |

OTHER PUBLICATIONS

Building Permit Application and Drawing—Dec. 16, 1986.
International Search Report for International Application No. PCT/US 00/31335 International Filing date Nov. 15, 2000.

* cited by examiner

Primary Examiner—Hien Tran
Assistant Examiner—Jennifer A. Leung

(57) ABSTRACT

An energy efficient series of mass and energy integrated reactive distillation columns and distillation columns are used to effect the production of diaryl carbonate. Utilizing the method or apparatus of the invention facilitates high diaryl carbonate production rates, and convenient recovery of unreacted starting materials and side-reaction products for recycle within the process for making diaryl carbonates or utilization in parallel reactions such as the manufacture of dialkyl carbonates. The method makes use of three reactive distillation columns and two rectification columns which are joined by a plurality of lines for transferring reactants and/or products into and out of the columns.

3 Claims, 2 Drawing Sheets ial carbonate and an aromatic alcohol in the presence of
METHOD AND APPARATUS FOR THE CONTINUOUS PRODUCTION OF DIARYL CARBONATES This is a divisional of application Ser. No. 09/457,320 filed on Dec. 8, 1999, now U.S. Pat. No. 6,294,684, which is incorporated herein by reference.

CROSS-REFERENCE TO RELATED APPLICATIONS

Not applicable.

FEDERALLY SPONSORED RESEARCH

Not applicable

BACKGROUND OF THE INVENTION

This application relates to the continuous production of diaryl carbonates by reaction of dialkyl carbonates and an aromatic alcohol in the presence of a catalyst.

Diaryl carbonates, such as diphenyl carbonate, are an important reactant in the production of polycarbonate resins. As the uses to which polycarbonates are put have increased, the efficient production of diaryl carbonates has become of greater significance. Early processes for the production of diaryl carbonates utilized phosgene as a reagent. The toxicity of phosgene, however, prompted the development of a non-phosgene process. As shown schematically in FIG. 1, the non-phosgene process involves a two-step process. First, a dialkyl carbonate such as dimethyl carbonate (DMC) reacts with an aromatic alcohol such as phenol to produce an alkyl aryl carbonate (e.g., phenylmethyl carbonate) and an alkyl alcohol (methanol). Then, in the second step, two molecules of the alkyl aryl carbonate undergo a transesterification reaction to produce one molecule of diaryl carbonate (diphenyl carbonate, DPC) and one molecule of dialkyl carbonate (DMC).

Various methods and apparatus for making diaryl carbonates are known in the art. For example, U.S. Pat. No. 5,210,268, which is incorporated herein by reference, relates to a process for continuously producing aromatic carbonates. The process is carried out in a distillation column, with product being recovered from the bottom of the column, and low boiling by-products being removed via the top of the column. Other processes for production of diaryl carbonates using a series of distillation columns are disclosed in U.S. Pat. Nos. 5,344,954 and 5,705,673 which are incorporated herein by reference.

The reaction shown in FIG. 1 is the reaction which is desired, but as is known to persons skilled in the art, there are number of side reactions which occur, producing unwanted by-products. These by-products can interfere with continuing production of the desired product, reduce the efficiency of the over-all process, and in some cases produce waste streams which require special handling for disposal. Thus, a significant challenge to the utilization of this process is the development of a process which minimizes the quantities and effects of the reaction by-products, while providing a good yield of the desired product.

The present invention provides a method for continuous production of diphenyl carbonate which has a high production rate while at the same time maintaining an energy efficient process. The present invention further provides an apparatus for continuous production of diphenyl carbonate which has a high production rate while at the same time maintaining an energy efficient process.

SUMMARY OF THE INVENTION

The invention is directed to a method and apparatus for continuous production of diaryl carbonates by reaction of a dialkyl carbonate and an aromatic alcohol in the presence of a transesterification catalyst. The method comprises the steps of:

(a) introducing reactant streams containing dialkyl carbonate, aromatic alcohol and transesterification catalyst to a first reactive distillation column to produce alkyl aryl carbonate and alkyl alcohol;

(b) recovering from the first reactive distillation column a first top stream containing dialkyl carbonate and alkyl alcohol and a first bottom stream containing alkyl aryl carbonate;

(c) introducing the first bottom stream into a second reactive distillation column to produce diaryl carbonate by disproportionation of the alkyl aryl carbonate;

(d) recovering from the second reactive distillation column a first side stream containing dialkyl carbonate and alkyl aryl ether and a second bottom stream containing diaryl carbonate, alkyl aryl carbonate and dialkyl carbonate;

(e) introducing the first side stream into a second rectification column to separate a dialkyl carbonate stream from the alkyl aryl ether, and recycling the dialkyl carbonate stream to the first rectification column;

(f) introducing the second bottom stream to a third reactive distillation column to further drive the reaction toward diaryl carbonate;

(g) recovering from the third reactive distillation column a second top stream containing unreacted aromatic alcohol, dialkyl carbonate and alkyl aryl ether and recycling the second top stream to the first reactive distillation column;

(h) introducing the first top stream into a first rectification column;

(i) recovering from the first rectification column an azeotrope top stream consisting essentially of dialkyl carbonate/alkyl alcohol azeotrope and a third bottom stream containing dialkyl carbonate, and recycling the third bottom stream to the first reactive distillation column; and (j) recovering a product stream containing essentially all of the diaryl carbonate produced from the bottom of the third reactive distillation column.

DETAILED DESCRIPTION OF THE INVENTION

The present invention provides an energy efficient series of mass and energy integrated reactive distillation columns and distillation columns to effect the production of diaryl carbonate. Utilizing the method or apparatus of the invention facilitates high diaryl carbonate production rates, and convenient recovery of unreacted starting materials and side-reaction products for recycle within the process for making diaryl carbonates or utilization in parallel reactions such as the manufacture of dialkyl carbonates.

Figure 1:
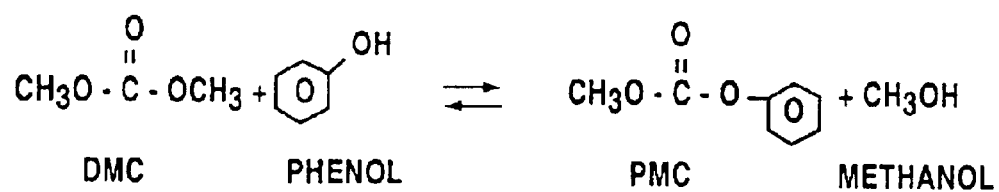
FIG. 1 shows the two-step reaction of dimethyl carbonate and phenol to produce diphenyl carbonate.
Figure 1:
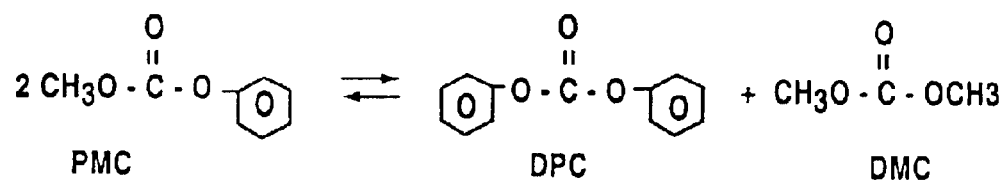

The principal reaction which is carried out in the method of the present invention is the reaction illustrated in FIG. 1.

It will be appreciated by persons skilled in the art that this process can be carried out using various dialkyl carbonates and various aromatic alcohols. Exemplary materials of each type are listed in the patents discussed above. Since the most common reactants used industrially are dimethyl carbonate and phenol, which react to produce diphenyl carbonate, however, these materials will be used as examples throughout the following discussion of the invention which follows. It should be understood, however, that this usage is merely for clarity of discussion, and that no limitation on the invention to the use of these specific materials is intended.

Figure 2:
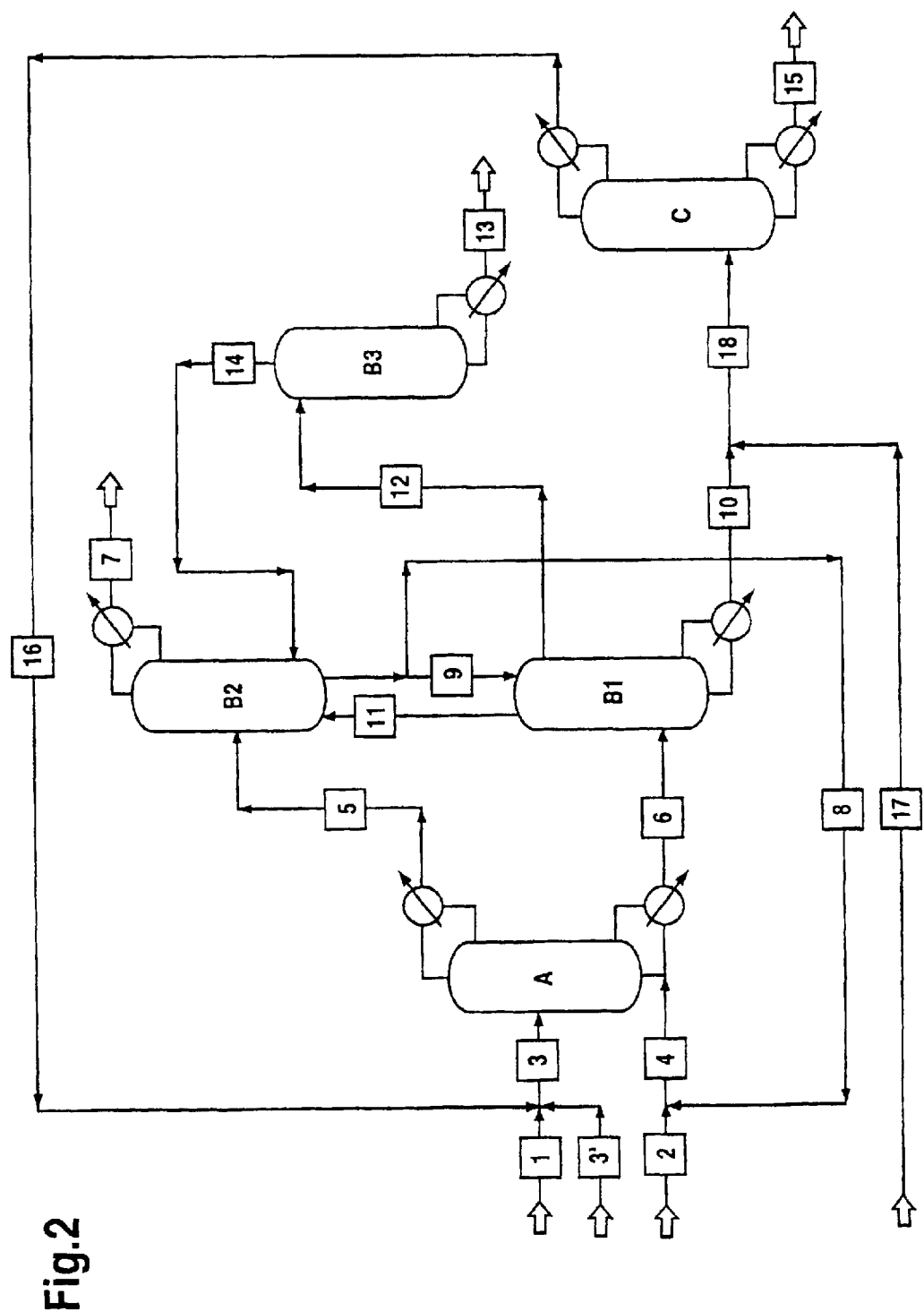
FIG. 2 shows an apparatus in accordance with the invention schematically.

FIG. 2 shows a schematic representation of the apparatus of the invention, including five columns A, B1, B2, B3 and C. Various feed, product and recycle streams indicated by the numbers 1–18.

Columns A, B1 and C are reactive/distillation columns. Thus, these columns each have a lower reaction section in which a chemical reaction occurs, and an upper rectification section. The construction of columns of this type are known in the art. In general, the reactive portion of the column will be furnished with arranged packings, dumped packings or fixed internals to provide at least three theoretical distillation stages. Preferably, the reactive section of Column A will provide 10 to 60, and more preferably 15 to 40, theoretical distillation steps.

Columns B2 and B3 are rectification columns. Thus, these columns are intended to carry out a separation of materials based upon boiling point, without driving a concurrent chemical reaction. The construction of columns of this type are known in the art.

The five columns illustrated in FIG. 2 are interconnected by a series of feed/recycle lines which serve to transport reactants and products. The direction of flow for each such line is indicated on FIG. 2. Various valves, heaters, and other fittings may be included with these feed/recycle lines in adapting the design to a particular installation, and the inclusion of such components is within the skill in the art.

The apparatus depicted in FIG. 2 can be utilized in accordance with the method of the invention to produce DPC. Starting materials are introduced to column A through as streams 3 and 4. Stream 3 is a combination of stream 1, which contains mainly phenol, either fresh or recycled, and stream 3' which contains phenol and catalyst. Optionally, stream 3 can also include DMC and side-reaction products recycled from reactive distillation column C via line 16. Stream 4 is a mixture of stream 2, containing mainly DMC and recycle stream 8 which contains mainly DMC and some minor amounts of phenol and side-reaction products recovered from the bottom of rectification column B2.

Stream 4 is fed into the bottom section of column A, preferably to the reboiler. The stream may be a liquid or a vapor, depending on the type of reboiler used. For example, if an external reboiler, e.g., a kettle reboiler, is used, stream 4 enters column A as a vapor. Stream 3 is fed as a liquid into the middle section of column A, at a location at the top of the reactive distillation section. The feed rate of streams 3 and 4 is such that the molar ratio of aromatic alcohol to dialkyl carbonate which is introduced into column A is between 0.1 and 10, preferably between 0.5 and 5 and most preferably between 1 and 3. It is particularly advantageous to provide dialkyl carbonate in excess through stream 4, since dialkyl carbonate serves as both a reactant and a stripping agent which facilitates removal of alkyl alcohol produced in the transesterification reaction. This removal increases the rate of production of alkyl aryl carbonate in column A.

The transesterification reaction in column A is carried out at a temperature from 100° C. to 300° C., preferably from 130° C. to 250° C., and most preferably from 140° C. to 220° C. The operating pressure at the top of column A is suitably in the range of 50 mbar to 20 bar, preferably 0.5 to 10 bar, and most preferably 3 to 7 bar.

Reaction products and unreacted starting materials are removed from column A in continuous manner through streams 5 and 6. Stream 5, which is drawn from the head of column A contains unreacted dialkyl carbonate and virtually all of the alkyl alcohol produced in the transesterification reaction. This stream is passed to rectification column B2 for processing and recovery. Stream 6 which is drawn from near the bottom of column A contains the alkyl aryl carbonate produced in column A, in combination with unreacted starting materials and catalyst. This stream 6 is passed to the second reactive distillation column B1.

Column B1 has a lower reaction section and an upper rectification section. This column promotes the disproportionation of alkyl aryl carbonate into diaryl carbonate and dialkyl carbonate, while at the same time separating dialkyl carbonate from the reaction mixture.

The reactive and rectification sections of column B1 are each furnished with arranged packings, dumped packings or fixed internals to provide 1 to 50, preferably 5 to 20 theoretical distillation steps. The temperature profile of column B1 ranges from 50 to 300° C., preferably 60 to 280° C., and most preferably 100 to 250° C.

The pressure in column B1 is maintained in the range of 50 mbar to 10 bar, preferably 0.2 to 5 bar, and most preferably 1 to 3 bar. It is desirable to maintain the pressure of column B1 below the pressure of column A. This results in an adiabatic flash of stream 6, hence facilitating disengagement of dialkyl carbonate from the reaction mixture.

Column B1 is operated in such a way that dialkyl carbonate entering the column through stream 6 is separated from the reaction mixture, hence increasing the rate of the disproportionation reaction taking place in the reactive section. Column B1 can also be utilized as a reboiler for column B2, in which case the two columns are connected by streams 9 and 11 as shown in FIG. 2. In this case, care should be taken to avoid carryover of alkyl aryl carbonate to column B2 in this configuration, since this could result in recycle of alkyl aryl carbonate to column A via stream 8. This would drive the composition in column A towards the starting materials, hence lowering the net production rate of alkyl aryl carbonate in column A. Thus, columns B1 and B2 are operated such that stream 9, when present, contains mainly dialkyl carbonate in the liquid phase, refluxing back from rectification column B2. Stream 11, when present, contains mainly dialkyl carbonate and the unwanted byproduct alkyl aryl ether (for example anisole) in the vapor phase. This provides most of the energy to drive the separation processes taking place in the column B2. Therefore, heat and mass integration is realized advantageously between columns B1 and B2 via streams 9 and 11.

Rectification column B2 produces a by-product stream 7 containing an azeotropic mixture of dialkyl carbonate and essentially all of the alkyl alcohol produced in the process. This stream can be condensed and reused as a feed stream for a complementary dialkyl carbonate production process without further purification.

Column B2 is furnished with arranged packings, dumped packings or fixed internals to provide at least 3 and preferably 5 to 50 theoretical distillation steps. The temperature profile of column B2 ranges from 10 to 200° C., preferably 50 to 150° C. The operating pressure in column B2 is in the range of 0.1 to 10 bar, preferably 0.5 to 2 bar.

In addition to streams 9 and 11 which interchange materials with column B2, materials leave column B1 via streams 10 and 12. Stream 12 contains mainly dialkyl carbonate and alkyl aryl ether and is drawn off as a side stream from column B1 and fed to a second rectification column B3. Column B3 separates dialkyl carbonate from alkyl aryl ethers, and returns the dialkyl carbonate to column B2 via line 14. The alkyl aryl ethers are discharged through line 13. This separation of alkyl aryl ethers such as anisole is important, since these products can build up within the apparatus if not removed.

Stream 10 contains the diaryl carbonate produced in column B1, in combination with unreacted starting materials, and some alkyl aryl carbonate and alkyl aryl ethers. Stream 10 is fed to reactive distillation column C, which is operated to further drive the reaction toward the desired diaryl carbonate product, while separating other materials for recycle. Two streams are removed from column C. The first is a product stream 15 which contains essentially all of the diaryl carbonate produced together with residual catalyst, some alkyl aryl carbonate and unwanted high boiling by-products. This product stream 15 may be further distilled if additional purification is desired. The second stream 16 is removed from the head of column C as a recycle stream containing essentially all of the unreacted aromatic alcohol starting material, and some dialkyl carbonate and alkyl aryl ether, and recycled to make up part of stream 3.

Column C is suitably operated at a temperature of from 100 to 300° C., preferably 100 to 250° C., and most preferably 140 to 200° C. The operating pressure in the column is suitably 10 mbar to 3 bar, preferably from 50 mbar to 1 bar, and most preferably from 100 to 400 mbar.

Within the scope of the process noted above, several variations are possible. Thus, as already described, the interconnection of columns B1 and B2 via streams 9 and 11 is optional although it provides improved efficiency. Similarly, stream 10 may be augmented by addition of a stream containing alkyl aryl carbonate via stream 17 to form stream 18. This results in an improvement in the overall production of diaryl carbonate. Suitably, stream 17 may be a alkyl aryl carbonate-containing stream recovered from the purification of diaryl carbonates.

The method as described above is suitably practiced in an apparatus in accordance with the invention. This apparatus comprises first, second and third reactive distillation columns, and first and second rectification column and a plurality of lines for transporting reactant and product streams, wherein:

(a) the first reactive distillation column is connected to input lines for the introduction of reactants, and to first and second transfer lines, said first transfer line running from the top of the first reactive distillation column to the middle of the first rectification column and the second transfer line running from the bottom of the first reactive distillation column to the second reactive distillation column (e.g., the bottom of the second reactive distillation column);

(b) the second reactive distillation column is connected to third and fourth transfer lines, said third transfer line running from the side of the second reactive distillation column to the top of the second rectification column, and said fourth transfer line running from the bottom of the second reactive distillation column to the third reactive distillation column (e.g. the bottom of the third reactive distillation column);

(c) the third reactive distillation column is connected to a first output line for providing diaryl carbonate product from the bottom of the third reactive distillation column and a first recycle line running from the top of the third reactive distillation column to the middle of the first reactive distillation column;

(d) the first rectification column is connected to a second product line for providing dialkyl carbonate/alkyl alcohol azeotrope from the top of the first rectification column, and a second recycle line running from the bottom of the first rectification column to the bottom of the first reactive distillation column; and (e) the second rectification column is connected to a third product line for recovering alkyl aryl ethers from the bottom of the second rectification column and a third recycle line running from the top of the second rectification column to the bottom of the first rectification column.

The apparatus may further comprise additional transfer lines running in opposing directions between the bottom of the first rectification column and the top of the second reactive distillation column and/or an augmentation line connected to the fourth transfer line for introduction of an augmenting reactant stream into the third reactive distillation column.

It will be appreciated by persons skilled in the art that the positioning of the various lines as described above as being in the top, middle or bottom of the column is necessarily a relative term since the position at which material is to be introduced is dependent on the conditions being maintained in the column. For example, a line entering the bottom of the column may actually enter a few stages above the sump, and a line entering the top of the column may enter a few stages below the top stage. Nonetheless, these terms are included to define the general orientation of the various columns and lines.

The method and apparatus of the invention allow the continuous production of diaryl carbonates via a catalyzed transesterification to proceed in a highly efficient manner on an industrial scale. The multistage process and apparatus of the invention provide production rates that are higher than those known in the art, and efficient separation and recycle (where appropriate) of unreacted starting materials and reaction by-products. Thus, the present invention represents an improvement over prior processes.

What is claimed is:

1. An apparatus for continuous production of diaryl carbonates by reaction of a dialkyl carbonate and an aromatic alcohol in the presence of a transesterification catalyst, said apparatus comprising: first, second and third reactive distillation columns, and a first rectification column and second rectification column and a plurality of lines for transporting reactant and product streams, wherein:

(a) the first reactive distillation column is connected to input lines for the introduction of reactants, and to first and second transfer lines, said first transfer line running from the top of the first reactive distillation column to the middle of the first rectification column and the second transfer line running from the bottom of the first reactive distillation column to the second reactive distillation column;

(b) the second reactive distillation column is connected to third and fourth transfer lines, said third transfer line running from the top of the second reactive distillation column to the top of the second rectification column, and said fourth transfer line running from the bottom of the second reactive distillation column to the third reactive distillation column;

(c) the third reactive distillation column is connected to a first output line for providing diaryl carbonate product from the bottom of the third reactive distillation column and a first recycle line running from the top of the third reactive distillation column to the middle of the first reactive distillation column;

(d) the first rectification column is connected to a second product line for providing dialkyl carbonate/alkyl alcohol azeotrope from the top of the first rectification column, and a second recycle line running from the bottom of the first rectification column to the bottom of the first reactive distillation column; and (e) the second rectification column is connected to a third product line for recovering alkyl aryl ethers from the bottom of the second rectification column and a third recycle line running from the top of the second rectification column to the bottom of the first rectification column, wherein a fifth and sixth transfer lines run in opposing directions between the bottom of the first rectification column and the top of the second reactive distillation column.

2. The apparatus of claim 1, wherein an augmentation line is connected to the fourth transfer line for introduction of an augmenting reactant stream into the third reactive distillation column.

3. The apparatus according to claim 1, wherein the first, second and third reactive distillation columns each comprise a reactive portion and a rectification portion, and wherein the reactive portion of each column contains packing or fixed internals effective to provide 10 to 60 theoretical distillation steps.

* * * * *